United States Patent [19]
Miyamoto et al.

[11] Patent Number: 5,962,535
[45] Date of Patent: Oct. 5, 1999

[54] COMPOSITION FOR ALZHEIMER'S DISEASE

[75] Inventors: Masaomi Miyamoto, Hyogo; Hiroyuki Ohta; Giichi Goto, both of Osaka, all of Japan

[73] Assignee: Takeda Chemical Industries, Ltd., Osaka, Japan

[21] Appl. No.: 09/042,625

[22] Filed: Mar. 17, 1998

Related U.S. Application Data

[63] Continuation-in-part of application No. PCT/JP98/00109, Jan. 14, 1998
[60] Provisional application No. 60/065,597, Nov. 18, 1997.

[30] Foreign Application Priority Data

Jan. 17, 1997 [JP] Japan ..................... 9-006147

[51] Int. Cl.$^6$ ............ A61K 31/045; A61K 31/12; A61K 31/55; A61K 31/445
[52] U.S. Cl. ............................................. 514/724
[58] Field of Search ...................... 514/724, 678, 514/211, 315, 431

[56] References Cited

U.S. PATENT DOCUMENTS

| | | | |
|---|---|---|---|
| 4,550,113 | 10/1985 | Lavretskaya et al. | 514/290 |
| 4,599,338 | 7/1986 | Regnier et al. | 514/265 |
| 4,895,841 | 1/1990 | Sugimoto et al. | 514/212 |
| 4,948,807 | 8/1990 | Rosin et al. | 514/484 |
| 5,059,627 | 10/1991 | Goto et al. | 514/688 |
| 5,273,974 | 12/1993 | Goto et al. | 514/221 |

FOREIGN PATENT DOCUMENTS

| | | |
|---|---|---|
| 0 629 400 A1 | 12/1994 | European Pat. Off. . |
| 1-221316 | 9/1989 | Japan . |

OTHER PUBLICATIONS

The Lancet, "Coenzyme $Q_{10}$, iron, and vitamin $B_6$ in genetically–confirmed Alzheimer's Disease", vol. 340, p. 671, Sep. 12, 1992.

*Primary Examiner*—Theodore J. Criares
*Attorney, Agent, or Firm*—Wenderoth, Lind & Ponack, L.L.P.

[57] ABSTRACT

A pharmaceutical composition comprising idebenone in combination with a compound having acetylcholinesterase inhibitory activity is useful for treating or preventing Alzheimer's disease.

5 Claims, 4 Drawing Sheets

[Fig. 1]
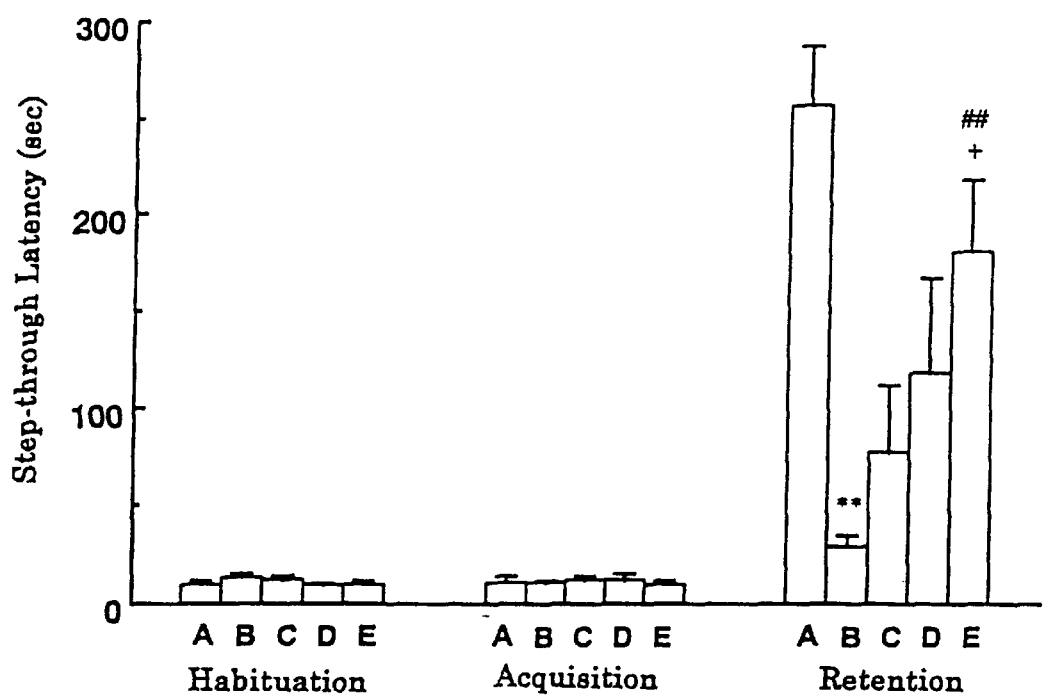
** P<0.01: Comparison to A (young rat group) (Mann-Whitney U test)
## P<0.01: Comparison to B (control group) (Mann-Whitney U tes)

[Fig. 2]
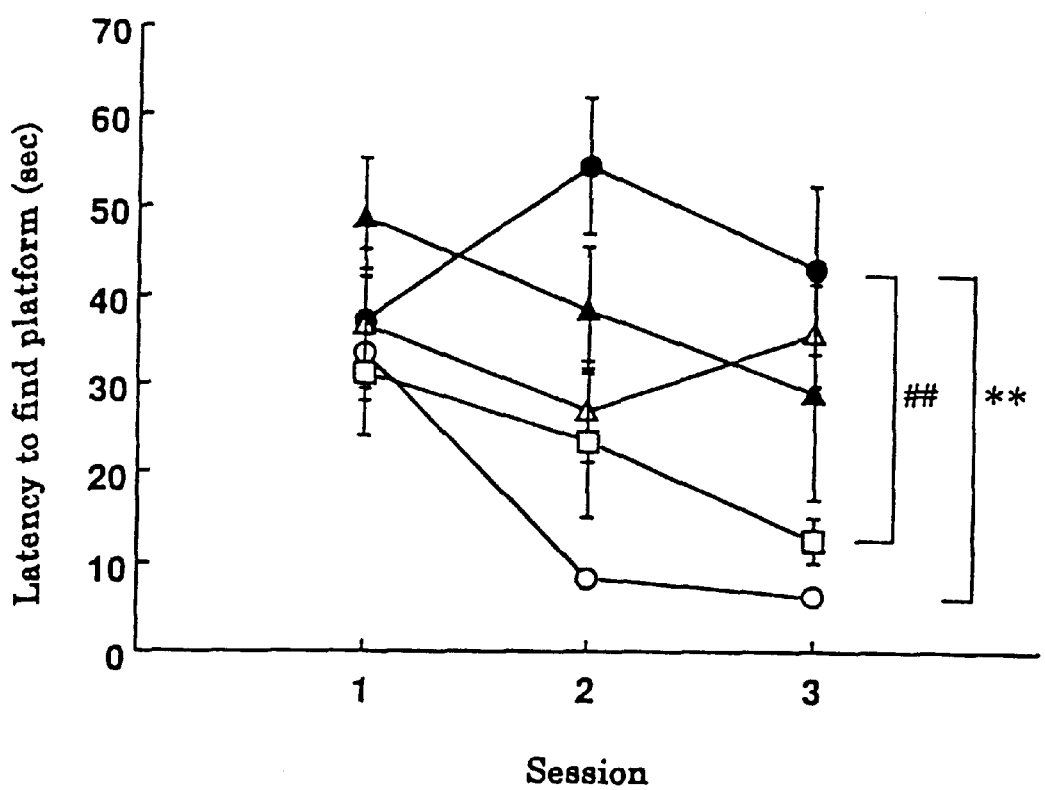
** P<0.01: Comparison to A (young rat group) (Dunnett test)
## P<0.01: Comparison to B (control group) (Dunnett test)

[Fig. 3]
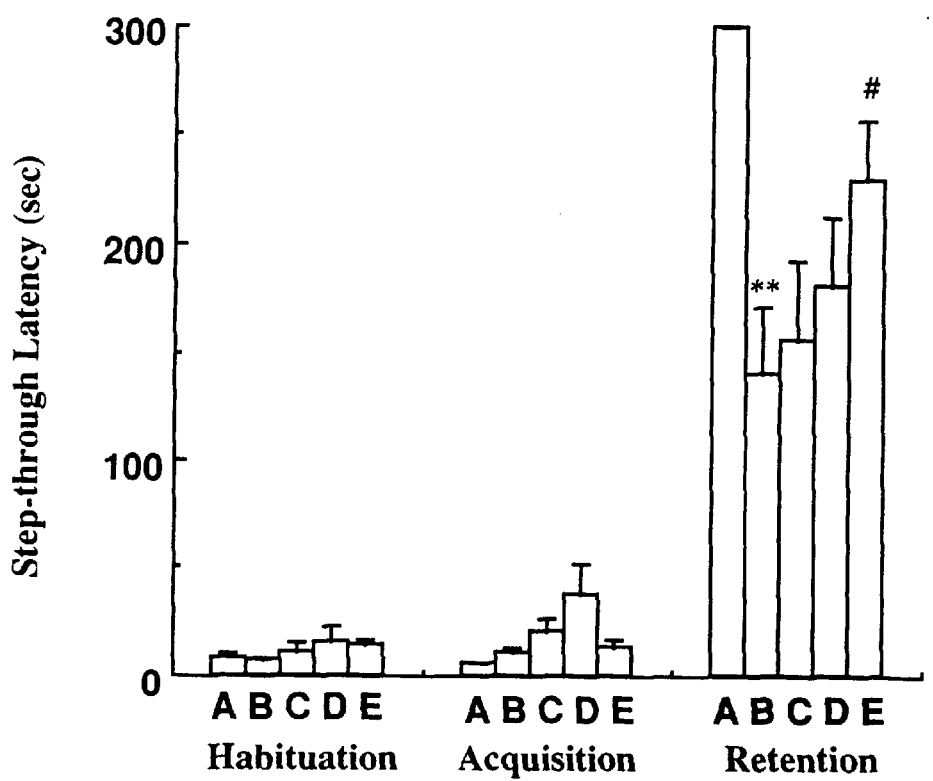
** P<0.01: Comparison to A (young rat group) (Mann-Whitney U test)
# P<0.05: Comparison to B (control group) (Mann-Whitney U test)

[Fig. 4]
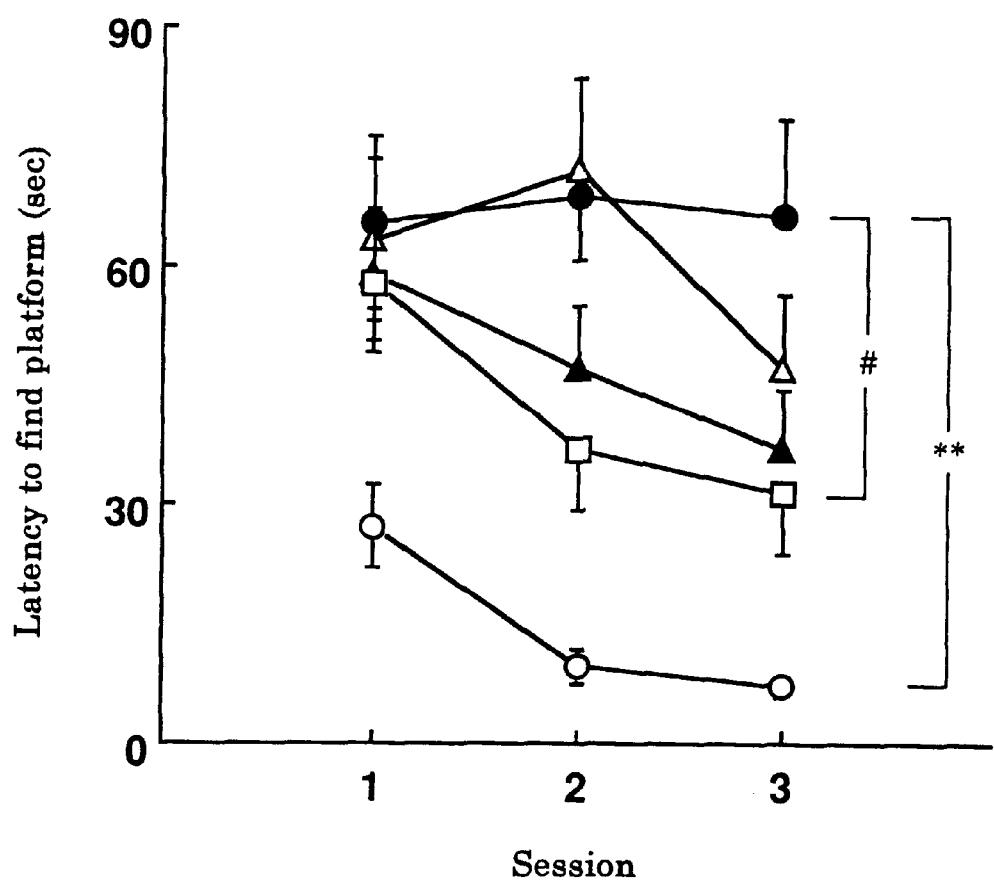
** P<0.01: Comparison to A (young rat group) (Dunnett test)
# P<0.05: Comparison to B (control group) (Dunnett test)

COMPOSITION FOR ALZHEIMER'S DISEASE

This application is a continuation-in-part of international application no. PCT/JP98/00109 filed Jan. 14, 1998, and this application claims the benefit of U.S. provisional application No. 60/065,597 filed Nov. 18, 1997.

TECHNICAL FIELD

The present invention relates to a pharmaceutical composition for treating or preventing Alzheimer's disease which comprises idebenone in combination with a compound having acetylcholinesterase inhibitory activity.

BACKGROUND ART

Alzheimer's disease is reportedly an organic brain disease with primary lesions within the brain and its etiology remains for the most part unraveled. However, the current knowledge suggests that Alzheimer's disease is a disease entity characterized by organic brain damages at least secondary to some preceding causative event, and the therapeutic modality so far proposed comprises curing the underlying disease inducing this organic disturbance of the brain or removing or otherwise disposing of the pathogenic factor or factors directly involved in the expression of such organic disturbance.

The underlying disease in Alzheimer's disease is multi-pronged, including cerebrovascular disorders (e.g. cerebral apoplexy associated with cerebral hemorrhage and infarction, hypertension, angitis, vascular anomaly, etc.), degenerative diseases (e.g. Pick's disease, Parkinson's disease, epilepsy, hydrocephalus, etc.), endocrine diseases (e.g. myxedema, Addison's disease, hypothyroidism, hypoglycemia, vitamin deficiencies, etc.), metabolic diseases (e.g. uremia, hepatic disorder, anoxia, etc.), intoxications (e.g. carbon monoxide poisoning, manganese poisoning, alcoholism, barbiturism, Korsakoff's syndrome, etc.), infectious diseases (e.g. chronic encephalitis), tumorigenic diseases (e.g. remote effects of cancer), and traumatic diseases (e.g. head injury).

Referring to the etiologic factors directly involved in the onset of Alzheimer's disease, the gene abnormality theory (Alzheimer gene, Down's syndrome gene, etc.), abnormal protein deposition theory [amyloid protein (senile plaque) theory, neurofibrillary tangle theory, etc.], and aluminum accumulation theory have been advanced.

The onset and progression of Alzheimer's disease is considered to arise from a complicated interaction of the above-mentioned underlying disease inducing Alzheimer's disease and the etiologic factor or factors directly inducing the expression of Alzheimer's disease.

JP-A-3 81218 (U.S. Pat. No. 5,059,627) reports that substituted 1,4-benzoquinone derivatives including idebenone and the corresponding hydroquinone derivatives have nerve growth factor secretion-inducing activity and are effective in the treatment of Alzheimer's disease.

JP-A-7 61923 (EP-A-629400) reports that high doses of idebenone are clinically effective in the therapy of senile dementia of Alzheimer type.

The Lancet, 340, 671(1992) reports that a combination therapy using coenzyme $Q_{10}$, an iron preparation, and vitamin $B_6$ is effective in the therapy and inhibition of progression of familial Alzheimer's disease.

JP-A-1 221316 discloses a nootropic composition comprising idebenone in combination with vinpocetine.

However, no report is available on a therapeutic or prophylactic medication for Alzheimer's disease that ever employs idebenone in combination with other medicinal substances.

For the method of treating and preventing Alzheimer's disease involving a multiplicity of etiologic factors as mentioned above, therapeutic drugs for the underlying diseases have been used independently for symptomatic relief only with limited success. Moreover, the only symptomatic remedy for Alzheimer's disease that has been available so far is tacrine (1,2,3,4-tetrahydro-9-acridinamine hydrochloride) and donepezil (2,3-dihydro-5,6-dimethoxy-2-[[1-(phenylmethyl)-4-piperidinyl]methyl]-1H-inden-1-one hydrochloride) which, however, have the drawback of hepatotoxicity and/or other cholinergic side effects.

BRIEF DESCRIPTION OF DRAWINGS

FIG. 1 is a diagrammatic representation of the ameliorating effect of idebenone-Compound A combination therapy on passive avoidance learning disturbance in aged rats, in which A represents the young rat group (saline), B represents the control group, C represents the Compound A group, D represents the idebenone group, and E represents the combination group.

FIG. 2 is a diagrammatic representation of the ameliorating effect of idebenone-Compound A (which is described hereinafter) combination therapy on water maze learning disturbance in aged rats, in which -○- represents the young rat group (saline), -●- represents the control group, -Δ- represents the Compound A group, -▲- represents the idebenone group, and -□- represents the combination group.

FIG. 3 is a diagrammatic representation of the ameliorating effect of idebenone-Compound B (which is described hereinafter) combination therapy on passive avoidance learning disturbance in aged rats, in which A represents the young rat group (saline), B represents the control group, C represents the Compound B group, D represents the idebenone group, and E represents the combination group.

FIG. 4 is a diagrammatic representation of the ameliorating effect of idebenone-Compound B combination therapy on water maze learning disturbance in aged rats, in which -0- represents the young rat group (saline), -●- represents the control group, -Δ- represents the Compound B group, -▲- represents the idebenone group, and -□- represents the combination group.

DISCLOSURE OF INVENTION

The inventors of the present invention did much research and found that a novel pharmaceutical mixture, combination dosage form, or concomitant pharmacotherapy which comprises idebenone in combination with at least one other medicinally active substance, particularly a compound having acetylcholinesterase inhibitory activity, as incorporated or used in a suitable combination, produces clinically beneficial effects as a medication exhibiting remarkable efficacy in the therapy (treating) and prophylaxis (preventing) of Alzheimer's disease and for inhibitory of the progression of Alzheimer's disease with substantially no risk for side effects and hence with greater safety than it is the case with the monotherapy using any of the above-mentioned active substances. The present invention has been developed on the basis of the above finding.

The present invention, therefore, is directed to a novel pharmaceutical composition for treating dementia or inhibiting the progression of dementia, and more particularly to a novel therapeutic and prophylactic composition which comprises idebenone in combination with a compound having acetylcholinesterase inhibitory activity as used in combination for the treatment or inhibition (slowdown) of progression of senile dementia of Alzheimer type and Alzheimer's disease.

The present invention relates to:

(1) A pharmaceutical composition for treating or preventing Alzheimer's disease which comprises idebenone in combination with a compound having acetylcholinesterase inhibitory activity;

(2) a composition of the above (1), wherein the compound having acetylcholinesterase inhibitory activity is a compound of the formula:

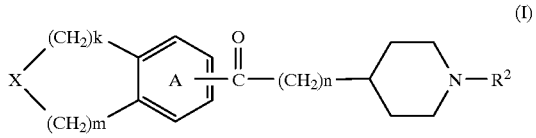

(I)

wherein X represents (i) $R^1$-N< wherein $R^1$ represents hydrogen, a hydrocarbon group which may be substituted or acyl which may be substituted, (ii) oxygen or (iii) sulfur; $R^2$ represents hydrogen or a hydrocarbon group which may be substituted; ring A represents a benzene ring which may be substituted; k represents an integer of 0 to 3; m represents an integer of 1 to 8; and n represents an integer of 1 to 6, or a salt thereof [hereinafter referred to briefly as compound (I)], (3) a composition of the above (1), wherein the compound having acetylcholinesterase inhibitory activity is 3-[1-(phenylmethyl)-4-piperidinyl]-1-(2,3,4,5-tetrahydro-1H-1-benzazepin-8-yl)-1-propanone fumarate, (4) a composition of the above (1), wherein the compound having acetylcholinesterase inhibitory activity is 2,3-dihydro-5,6-dimethoxy-2-[[1-(phenylmethyl)-4-piperidinyl]methyl]-1H-inden-1-one hydrochloride, (S)-3-[1-(dimethylamino)ethyl]phenyl N-ethyl-N-methylcarbamate or 9-amino-2,3,5,6,7,8-hexahydro-1H-cyclopenta[b]quinoline, (5) a pharmaceutical composition for inhibiting the progression of dementia which comprises which comprises idebenone in combination with a compound having acetylcholinesterase inhibitory activity, (6) a method for treating or preventing Alzheimer's disease in mammal, which comprises administering to such mammal an effective amount of idebenone in combination with a compound having acetylcholinesterase inhibitory activity, (7) use of idebenone in combination with a compound having acetylcholinesterase inhibitory activity for the manufacture of a composition for treating or preventing Alzheimer's disease, and so forth.

Idebenone, which is used in accordance with the present invention, is the generic name of the compound described in, for example, JP-B-62 3134 (1987), U.S. Pat. No. 4,139,545, etc. It's chemical name is 6-(10-hydroxydecyl)-2,3-dimethoxy-5-methyl-1,4-benzoquinone.

The active substance which is used in combination with idebenone can be virtually any substance that can be used in the treatment or prevention of Alzheimer's disease. Preferred are compounds having acetylcholinesterase inhibitory activity.

The compound having acetylcholinesterase inhibitory activity includes, for example, the following compounds.

1) 1,2,3,4-Tetrahydro-9-aminoacridinamine hydrochloride (tacrine) [The New England Journal of Medicine, 327, 1253–1259, 1992].

2) The compound (I) described in JP-A-5 140149 or U.S. Pat. No. 5,273,974.

Referring to the above formula (I), "hydrocarbon group" of the "hydrocarbon group which may be substituted" as defined for $R^1$ and $R^2$ includes, for example, alkyl, alkenyl, alkynyl, cycloalkyl, bridged cyclic saturated hydrocarbon group, aryl, aralkyl, arylalkenyl, arylalkynyl, cycloalkylalkyl, etc.

The alkyl includes, for example, $C_{1-11}$ alkyl (e.g. methyl, ethyl, n-propyl, i-propyl, n-butyl, i-butyl, tert-butyl, n-pentyl, n-hexyl, etc.).

The alkenyl includes, for example, straight-chain or branched $C_{2-4}$ alkenyl (e.g. vinyl, allyl, 2-butenyl, etc.).

The alkynyl includes, for example, $C_{2-4}$ alkynyl (e.g. propargyl, 2-butynyl, etc.).

The cycloalkyl includes, for example, $C_{3-7}$ cycloalkyl (e.g. cyclopropyl, cyclobutyl, cyclopentyl, cyclohexyl, etc.).

The bridged cyclic saturated hydrocarbon group includes, for example, $C_{8-14}$ bridged saturated alicyclyl (e.g. bicyclo[3.2.1]oct-2-yl, bicyclo[3.3.1]non-2-yl, adamantan-1-yl, etc.).

The aryl includes, for example, $C_{6-10}$ aryl (e.g. phenyl, naphthyl, etc.).

The aralkyl includes, for example, $C_{7-18}$ aralkyl (e.g. phenyl-$C_{1-12}$ alkyl and a-naphthyl-$C_{1-8}$ alkyl, such as phenylmethyl, phenylethyl, phenylpropyl, phenylbutyl, phenylpentyl, phenylhexyl, a-naphthylmethyl, etc.).

The arylalkenyl includes, for example, $C_{8-18}$ arylalkenyl (e.g. phenyl-$C_{2-12}$ alkenyl such as styryl, cinnamyl, 4-phenyl-2-butenyl, 4-phenyl-3-butenyl, etc.).

The arylalkynyl includes, for example, $C_{8-18}$ arylalkynyl (e.g. phenyl-$C_{2-12}$ alkynyl such as phenylethynyl, 3-phenyl-2-propynyl, 3-phenyl-1-propynyl, etc.).

The cycloalkylalkyl includes, for example, $C_{3-7}$ cycloalkyl-$C_{1-6}$ alkyl (e.g. cyclopropylmethyl, cyclobutylmethyl, cyclopentylmethyl, cyclohexylmethyl, cycloheptylmethyl, cyclopropylethyl, cyclobutylethyl, cyclopentylethyl, cyclohexylethyl, cycloheptylethyl, cyclopropylbutyl, cyclobutylbutyl, cyclopentylbutyl, cyclohexylbutyl, cycloheptylbutyl, cyclopropylpentyl, cyclobutylpentyl, cyclopentylpentyl, cyclohexylpentyl, cycloheptylpentyl, cyclopropylhexyl, cyclobutylhexyl, cyclopentylhexyl, cyclohexylhexyl, cycloheptylhexyl, etc.).

The substituent for the "hydrocarbon group which may be substituted" as defined for $R^1$ or $R^2$ includes, for example, $C_{1-4}$ alkyl (e.g. methyl, ethyl, propyl, butyl, etc.), halo-$C_{1-4}$ alkyl (e.g. trifluoromethyl, pentafluoroethyl, etc.), halogen (e.g. fluoro, chloro, bromo, iodo, etc.), nitro, cyano, hydroxy, $C_{1-4}$ alkoxy (e.g. methoxy, ethoxy, propyloxy, butyloxy, isopropyloxy, etc.), mercapto, $C_{1-4}$ alkylthio (e.g. methylthio, ethylthio, propylthio, isopropylthio, butylthio, etc.), amino, mono- or di-$C_{1-4}$ alkylamino (e.g. methylamino, ethylamino, propylamino, dimethylamino, diethylamino, etc.), 5- to 7-membered cyclic amino (e.g. pyrrolidino, piperidino, morpholino, thiomorpholino, etc.), formyl, $C_{1-4}$ alkyl-carbonyl (e.g. acetyl, propionyl, etc.), $C_{1-4}$ alkyl-carbonylamino (e.g. acetylamino, propionylamino, butyrylamino, etc.), aminocarbonyloxy, mono- or di-$C_{1-4}$ alkylamino-carbonyloxy (e.g. methylaminocarbonyloxy, ethylaminocarbonyloxy, dimethylaminocarbonyloxy, diethylaminocarbonyloxy, methylethylaminocarbonyloxy, etc.), $C_{1-4}$ alkylsulfonylamino (e.g. methylsulfonylamino, ethylsulfonylamino, propylsulfonylamino, etc.), $C_{1-4}$ alkoxy-carbonyl (e.g.

methoxycarbonyl, ethoxycarbonyl, propoxycarbonyl, isobutoxycarbonyl, etc.), hydroxycarbonyl, $C_{1-6}$ alkyl-carbonyl (e.g. methylcarbonyl, ethylcarbonyl, butylcarbonyl, etc.), $C_{3-6}$ cycloalkylcarbonyl (e.g. cyclopentylcarbonyl, cyclohexylcarbonyl, etc.), carbamoyl, thiocarbamoyl, mono- or di-$C_{1-4}$ alkylcarbamoyl (e.g. methylcarbamoyl, ethylcarbamoyl, propylcarbamoyl, butylcarbamoyl, diethylcarbamoyl, dibutylcarbamoyl, etc.), $C_{1-6}$ alkylsulfonyl (e.g. methylsulfonyl, ethylsulfonyl, propylsulfonyl, etc.), $C_{3-6}$ cycloalkylsulfonyl (e.g. cyclopentylsulfonyl, cyclohexylsulfonyl, etc.), $C_{6-10}$ aryl (e.g. phenyl, naphthyl, etc.), $C_{6-10}$ aryloxy (e.g. phenoxy etc.), $C_{6-10}$ aryl-carbonyl (e.g. benzoyl etc.), $C_{6-10}$ aryloxy-carbonyl (e.g. phenoxycarbonyl etc.), $C_{7-11}$ aralkyl-carbamoyl (e.g. benzylcarbamoyl etc.), $C_{6-10}$ aryl-carbamoyl (e.g. phenylcarbamoyl etc.), $C_{7-11}$ aralkyl-carbonylamino (e.g. benzylcarbonylamino etc.), $C_{6-10}$ aryl-carbonylamino (e.g. benzoylamino etc.), $C_{7-11}$ aralkylsulfonyl (e.g. benzylsulfonyl etc.), $C_{6-10}$ arylsulfonyl (e.g. phenylsulfonyl etc.), $C_{7-11}$ aralkylsulfinyl (e.g. phenyl-sulfinyl etc.), $C_{6-10}$ arylsulfonylamino (e.g. phenylsulfony-lamino etc.), and so forth. The above-mentioned $C_{6-10}$ aryl, $C_{6-10}$ aryloxy, $C_{6-10}$ aryl-carbonyl, $C_{6-10}$ aryl-oxycarbonyl, $C_{7-11}$ aralkyl-carbamoyl, $C_{6-10}$-aryl-carbamoyl, $C_{7-11}$ aralkyl-carbonylamino, $C_{6-10}$ aryl-carbonylamino, $C_{7-11}$ aralkylsulfonyl, $C_{6-10}$ arylsulfonyl, $C_{7-11}$ aralkylsulfinyl, and $C_{6-10}$ arylsulfonylamino may each have 1 to 4 substituents such as $C_{1-4}$ alkyl, $C_{1-4}$ alkoxy, halogen, hydroxy, $C_{7-11}$ aralkyloxy, amino, mono- or di-$C_{1-4}$ alkylamino, nitro, and $C_{1-4}$ alkylcarbonyl, among others.

The "hydrocarbon group which may be substituted" may have 1 to 5 substituents such as those mentioned above on its suitable position(s).

The "hydrocarbon group" of the "hydrocarbon group which may be substituted" as defined for $R^1$ is preferably straight-chain or branched $C_{1-7}$ alkyl (e.g. methyl, ethyl, propyl, isopropyl, butyl, isobutyl, tert-butyl, pentyl, hexyl, etc.), $C_{7-10}$ aralkyl (e.g. benzyl, phenylethyl, phenylpropyl, etc.), among others.

The "hydrocarbon group" of the "hydrocarbon group which may be substituted" is preferably $C_{7-10}$ aralkyl (e.g. phenylmethyl, phenylethyl, phenylpropyl, etc.), among others.

The "acyl" of the "acyl which may be substituted" as defined for $R^1$ includes, for example, carboxylic acid-derived acyl, sulfonic acid-derived acyl, phosphoric acid-derived acyl, and substituted oxycarbonyl.

The carboxylic acid-derived acyl includes, for example, formyl, $C_{1-6}$ alkyl-carbonyl (e.g. acetyl, propionyl, butyryl, etc.) and $C_{6-10}$ aryl-carbonyl (e.g. benzoyl etc.).

The sulfonic acid-derived acyl includes, for example, $C_{1-6}$ alkylsulfonyl (e.g. methanesulfonyl, ethanesulfonyl, propanesulfonyl, etc.) and $C_{6-10}$ arylsulfonyl which may be substituted by $C_{1-4}$ alkyl (e.g. phenylsulfonyl, p-toluenesulfonyl, etc.).

The phosphoric acid-derived acyl includes, for example, $C_{1-6}$ alkylphosphonyl (e.g. methanephosphonyl, ethanephosphonyl, propanephosphonyl, etc.) and $C_{6-10}$ arylphosphonyl (e.g. phenylphosphonyl etc.).

The substituted oxycarbonyl includes, for example, $C_{1-6}$ alkoxy-carbonyl (e.g. methoxycarbonyl, tert-butoxycarbonyl, etc.) and $C_{7-11}$ aralkyloxy-carbonyl (e.g. benzyloxycarbonyl etc.). Among others, preferred is $C_{1-6}$ alkyl-carbonyl.

The substituent for the "acyl which may be substituted" for R includes, for example, halogen, amino, mono- or di-$C_{1-6}$ alkylamino, and $C_{1-4}$alkoxy. This acyl may have 1 to 3, preferably 1 or 2, substituents such as those mentioned above in its substitutable position or positions.

The "benzene ring which may be substituted" for ring A in the formula (I) may have 1 to 3 substituents selected from among the substituents mentioned above for the "hydrocarbon group which may be substituted" of $R^1$.

X is preferably $R^1$-N<.

$R^1$ is preferably hydrogen, straight-chain or branched $C_{1-3}$ alkyl (e.g. methyl, ethyl, propyl, isopropyl, etc.), $C_{7-11}$ aralkyl (e.g. benzyl etc.), $C_{6-10}$ aryl (e.g. phenyl etc.), $C_{1-3}$ alkyl-carbonyl (e.g. acetyl, propionyl, butyryl, etc.), $C_{6-10}$ aryl-carbonyl (e.g. benzoyl etc.), $C_{1-3}$ alkoxy-carbonyl (e.g. methoxycarbonyl, ethoxycarbonyl, etc.), and so forth.

$R^2$ is preferably $C_{7-11}$ aralkyl which may be substituted by 1 to 2 substituents selected from the group consisting of halogen, $C_{1-3}$ alkyl (e.g. methyl etc.), nitro, and $C_{1-3}$ alkoxy (e.g. methoxy), [e.g. benzyl, a-naphthylmethyl, etc.]. Particularly preferred is benzyl.

The preferred substituent group on ring A includes halogen (e.g. fluoro, chloro, etc.), $C_{1-3}$alkyl (e.g. methyl etc.), halo-$C_{1-3}$ alkyl (e.g. trifluoromethyl etc.), $C_{1-3}$ alkoxy (e.g. methoxy etc.), among others. Particularly preferred is fluoro.

k and m are preferably such that the sum of k and m (k+m) is an integer of 2 to 6; that is to say, the ring of the formula:

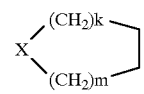

is preferably a 5- to 9-membered ring. Preferred specific combinations of k and m are such that when k is 0, m is 2, 3, 4, or 5; when k is 1, m is 1, 2, or 3; and when k is 2, m is 2.

The nitrogen-containing fused heterocyclic ring of the formula:

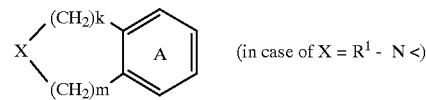

preferably includes 2,3-dihydro-1H-indole, 1,2,3,4-tetrahydroquinoline, 2,3,4,5-tetrahydro-1H-1-benzazepine, 2,3-dihydro-1H-isoindole, 1,2,3,4-tetrahydroisoquinoline, 2,3,4,5-tetrahydro-1H-2-benzazepine, 2,3,4,5-tetrahydro-1H-3-benzazepine, 1,2,3,4,5,6-hexahydro-1-benzazocine, 1,2,3,4,5,6-hexahydro-2-benzazocine, 1,2,3,4,5,6-hexahydro-3-benzazocine, 2,3,4,5,6,7-hexahydro-1H-1-benzazonine, 2,3,4,5,6,7-hexahydro-1H-2-benzazonine, 2,3,4,5,6,7-hexahydro-1H-3-benzazonine, 2,3,4,5,6,7-hexahydro-1H-4-benzazonine, among others.

The oxygen-containing fused heterocyclic ring of the formula:

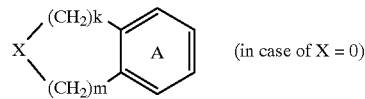

preferably includes 2,3-dihydrobenzofuran, 1,3-dihydroisobenzofuran, 3,4-dihydro-2H-1-benzopyran, 3,4-dihydro-1H-2-benzopyran, 2,3,4,5-tetrahydro-1-benzoxepine, 1,3,4,5-tetrahydro-2-benzoxepine, 1,2,4,5-tetrahydro-3-benzoxepine, 3,4,5,6-tetrahydro-2H-1-benzoxocine, 3,4,5,6-tetrahydro-1H-2-benzoxocine, 1,4,5,6- tetrahydro-2H-3-benzoxocine, 2,3,4,5,6,7-hexahydro-1-benzoxonine, 1,3,4,5,6,7-hexahydro-2-benzoxonine, 1,2,4,5,6,7-hexahydro-3-benzoxonine, 1,2,3,5,6,7-hexahydro-4-benzoxonine, among others.

The sulfur-containing fused heterocyclic ring of the formula:

 (in case of X = S)

preferably includes 2,3-dihydro[b]thiophene, 1,3-dihydrobenzo[c]thiophene, 3,4-dihydro-2H-1-benzothiopyran, 3,4-dihydro-1H-2-benzothiopyran, 2,3,4,5-tetrahydro-1-benzothiepine, 1,3,4,5-tetrahydro-2-benzothiepine, 1,2,4,5-tetrahydro-3-benzothiepine, 3,4,5,6-tetrahydro-2H-1-benzothiocine, 3,4,5,6-tetrahydro-1H-2-benzothiocine, 1,4,5,6-tetrahydro-2H-3-benzothiocine, 2,3,4,5,6,7-hexahydro-1-benzothionine, 1,3,4,5,6,7-hexahydro-2-benzothionine, 1,2,4,5,6,7-hexahydro-3-benzothionine, and 1,2,3,5,6,7-hexahydro-4-benzothionine, among others.

The preferred fused heterocyclic ring of the formula:

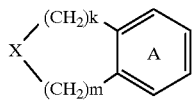

includes, for example, the nitrogen-containing fused heterocyclic ring of the formulas:

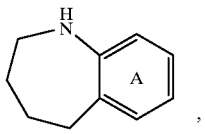,

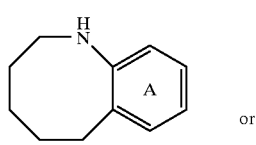 or

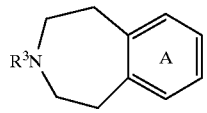

wherein $R^3$ represents hydrogen or $C_{1-3}$ alkyl.

The $C_{1-3}$ alkyl for $R^3$ includes, for example, methyl, ethyl, propyl, isopropyl, among others.

n is preferably 1, 2, or 3 and more preferably is 2.

To be more specific, the preferred compound (I) includes those in which

X is (i) $R^1$-N< wherein $R^1$ is hydrogen, $C_{1-6}$ alkyl, $C_{2-4}$ alkyl-carbonyl or $C_{7-11}$ aralkyl, or (ii) oxygen;

$R^2$ is (1) hydrogen or (2) benzyl which may be substituted by 1 or 2 substituents selected from the group consisting of halogen, $C_{1-3}$ alkyl, nitro and $C_{1-3}$ alkoxy;

ring A is a benzene ring; and the sum of k and m (k+m) is an integer of 2 to 5.

The salt of compound of formula (I) is preferably a physiologically acceptable salt. The salt includes acid addition salts such as salts with inorganic acids (e.g. hydrochloric acid, phosphoric acid, hydrobromic acid, sulfuric acid, etc.) and salts with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.). Where the compound has an acidic group such as -COOH, it may form salts with inorganic bases (e.g. sodium, potassium, calcium, magnesium, ammonia, etc.) or organic bases (e.g. triethylamine etc.).

Compound (I) is preferably 3-[1-(phenylmethyl)-4-piperidinyl]-1-(2,3,4,5-tetrahydro-1H-1-benzazepin-8-yl)-1-propanone fumarate.

3) The cyclic amine derivative of the following formula or a pharmacologically acceptable salt as described in JP-A-64 79151 or U.S. Pat. No. 4,895,841.

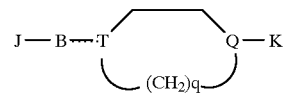

wherein J represents (a) a group, substituted or unsubstituted, selected from the group consisting of (1) phenyl, (2) pyridyl, (3) pyrazyl, (4) quinolyl, (5) cyclohexyl, (6) quinoxalyl and (7) furyl;

(b) amonovalent or divalent group, in which the phenyl have a substituent(s) selected from the group consisting of (1) indanyl, (2) indanonyl, (3) indenyl, (4) indenonyl, (5) indanedionyl, (6) tetralonyl, (7) benzosuberonyl, (8) indanolyl and (9) a group of the formula $C_6H_5$—CO—CH($CH_3$)—;

(c) a monovalent group derived from a cyclic amide compound;

(d) a lower alkyl group or (e) a group of the formula: $R_1$—CH=CH— wherein $R_1$ represents hydrogen or lower alkoxycarbonyl;

B represents a group of the formula: —(CHR$_2$)n— or —CO—(CHR$_2$)n—, a group of the formula: —NR$_3$—(CHR$_2$)n— wherein R$_3$ represents hydrogen, lower alkyl, acyl, lower alkylsulfonyl, phenyl which may be substituted or benzyl, a group of the formula: —CO—NR$_4$—(CHR$_2$)n— wherein R$_4$ represents hydrogen, lower alkyl or phenyl, a group of the formula: —CH=CH—(CHR$_2$)n—, a group of the formula: —OCOO—(CHR$_2$)n—, a group of the formula: —O—CO—NH—(CHR$_2$)n—, a group of the formula: —NH—CO—(CHR$_2$)n—, a group of the formula: —CH$_2$—CO—NH—(CHR$_2$)n—, a group of the formula: —(CH$_2$)$_2$—CO—NH—(CHR$_2$)n—, a group of the formula: —CH(OH)—(CHR$_2$)n— in the above formulas, n represents 0 or an integer of 1 to 10; R$_2$ represents hydrogen or methyl so that the alkylene group of the formula: —(CHR$_2$)n— is unsubstituted or has one or more methyl groups, a group of the formula: =(CH—CH=CH)$_b$— wherein b represents an integer of 1 to 3, a group of the formula: =CH—(CH$_2$)$_c$— wherein c represents 0 or an integer of 1 to 9, a group of the formula: =(CH—CH)$_d$= wherein d represents an integer of 1 to 5, a group of the formula: —CO—CH=CH—CH$_2$—, a group of the formula: —CO—CH$_2$—CH(OH)—CH$_2$—, a group of the formula: —CH(CH$_3$)—CO—NH—CH$_2$—, a group of the formula: —CH=CH—CO—NH—(CH$_2$)$_2$—, a group of the formula: —NH—, a group of the formula: —O—, a group of the formula: —S—, dialkylaminoalkylcarbonyl or lower alkoxycarbonyl;

T represents nitrogen or carbon;

Q represents nitrogen, carbon, or a group of the formula: >N→O;

K represents hydrogen, substituted or unsubstituted phenyl, arylalkyl in which the phenyl may be substituted, cinnamyl in which the phenyl may be substituted, lower alkyl, pyridylmethyl, cycloalkylalkyl, adamantanemethyl, furylmethyl, cycloalkyl, lower alkoxycarbonyl or acyl;

q represents an integer of 1 to 3.

Among them, the preferred is 2,3-dihydro-5,6-dimethoxy-2-[[1-(phenylmethyl)-4-piperidinyl]methyl]-1H-inden-1-one hydrochloride (Donepezil, E2020).

4) 9-Amino-2,3,5,6,7,8-hexahydro-1H-cyclopenta[b]quinoline (Ipidacrine) [JP-A-59 55830, U.S. Pat. No. 4,550,113].

5) The compound of the following formula or a pharmacologically acceptable salt thereof as described in JP-A-61 225158 or U.S. Pat. No. 4,948,807.

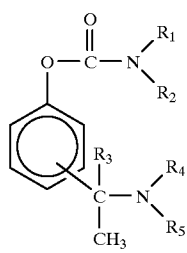

wherein $R_1$ represents hydrogen, lower alkyl, cyclohexyl, allyl, or benzyl; $R_2$ represents hydrogen, methyl, ethyl or propyl; or $R^1$ and $R^2$ form, taken together with the adjacent nitrogen atom, represent morpholino or piperidino; $R_3$ represents hydrogen or lower alkyl; $R_4$ and $R_5$ may be the same or different and each represents lower alkyl; the dialkylaminoalkyl group is located in the meta-, ortho-, or para-position.

Among others, preferred is (S)-3-[1-(dimethylamino)ethyl]phenyl N-ethyl-N-methylcarbamate (Rivastigmin, SDZ-ENA-713).

6) A xanthine compound of the following formula or a physiologically acceptable acid addition salt thereof as described in JP-A-60 174788 or U.S. Pat. No. 4,599,338.

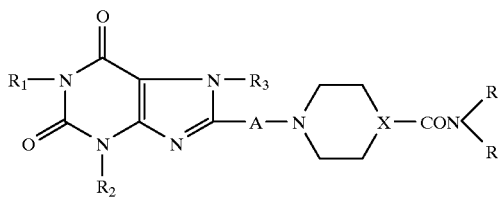

wherein $R^1$ is selectedfrom the group consisting of hydrogen and straight-chain or branched $(C_1-C_5)$alkyl; $R^2$ is selected from the group consisting of hydrogen, straight-chain or branched $(C_1-C_5)$alkyl, straight-chain or branched $(C_1-C_5)$ alkyl containing a double bond, and benzyl; $R^3$ is selected from the group consisting of hydrogen and methyl; A is selected from the group consisting of polymethylene chains of $(CH_2)n$ wherein n is an integer of 1 to 4 and such chains substituted, where n is larger than 1, by a hydroxy; X is selected from the group consisting of nitrogen and >CH—NH—; the substituents represented by R are each selected from the group consisting of $C_{1-5}$ alkyl groups or joined together, two Rs are selected from the group consisting of $C_{4-6}$ polymethylene chains and such chains containing one hetero atom selected from ha group consisting of oxygen and sulfur in order to form with the adjacent nitrogen atom a heterocyclic group containing one or two hetero atoms.

Among others, the preferred is 8-[3-[4-(diethylcarbamoyl)piperazin-1-yl]propyl]-1,3,7-trimethylxanthine hydrochloride (Stacofylline, S-9977).

7) 4a,5,9,10,11,12-Hexahydro-3-methoxy-11-methyl-6-H-benzofuro[3a,3,2-ef][2]benzazepin-6-ol (Galanthamine) [e.g. European Journal of Medicinal Chemistry, 27, 565–570 (1992); Psychopharmacology, 121, 164–172 (1995)].

8) Dimethyl (2,2,2-trichloro-1-hydroxyethyl) phosphonate (Metrifonate) [e.g. Journal of Cerebral Blood Flow and Metabolism, 16, 1014–1025 (1996)].

The preferred example of the combination of idebenone and a compound having acetylcholinesterase inhibitory activity is the combination of idebenone with 3-[1-(phenylmethyl)-4-piperidinyl]-1-(2,3,4,5-tetrahydro-1-H-1-benzazepin-8-yl)-1-propanone fumarate. Also preferred is the combination of idebenone with donepezil.

The pharmaceutical composition for treating or preventing Alzheimer's disease or the pharmaceutical composition for inhibiting the progression of dementia, of the present invention comprise idebenone in combination with a compound having acetylcholinesterase inhibitory activity as active ingredients. This composition can be used orally in the form of a dosage form available on mixing each of the above compounds (active ingredients) with a pharmacologically acceptable carrier or excipient and then combining them.

The pharmaceutical composition for treating or preventing Alzheimer's disease or the pharmaceutical composition for inhibiting the progression of dementia, of the present invention can be provided, for example, in the alternative forms prepared by the following procedures. (1) the above compounds are mixed optionally with a pharmaceutically acceptable excipient or the like by the known pharmaceutical technology to provide one dosage form, (2) the respective compounds are independently processed, optionally together with a pharmaceutically acceptable excipient or the like, to use in combination with independent dosage forms, or (3) the respective compounds are independently processed, optionally together with a pharmaceutically acceptable exclpient or the like, to provide independently prepared dosage forms as a set.

In the pharmaceutical composition of the present invention, in case that the respective compounds are independently processed to provide independently prepared dosage forms, they can be administered to one patient or prospective patient at one and the same time or at staggered times, and the numbers of dosing of the respective dosage forms may not be equal.

The pharmaceutical composition for treating or preventing Alzheimer's disease or the pharmaceutical composition for inhibiting the progression of dementia, of the present invention can be provided in any and all dosage forms that can be administered to patients by the oral route, such as tablets, fine granules, capsules, and granules, among others. Preferred are tablets, fine granules, and capsules.

The pharmaceutical composition of the present invention can be manufactured by theper se known procedures or any those analogous thereto, using the common excipient, binder, disintegrator, lubricant, and/or other formulation additives.

The excipient includes, for example, sucrose, lactose, glucose, starch, mannitol, sorbitol, cellulose, talc, and cyclodextrins. The binder includes, for example, cellulose, methylcellulose, polyvinylpyrrolidone, gelatin, gum arabic, polyethylene glycol, sucrose, and starch. The disintegrator includes, for example, starch, carboxymethylcellulose, and carboxymethylcellulose calcium. The lubricant includes, for example, talc, etc.

Where necessary, the composition can be provided in sustained release dosage forms. The dosage forms can be manufactured by the per se known technology, for example, by coating the tablets, granules, fine granules, capsules, etc. with the common oleaginous substance (e.g. triglycerides), polyglycerol fatty acid esters, hydroxypropylcellulose, etc.

The pharmaceutical composition containing idebenone, for instance, can be provided in various dosage forms (e.g. tablets, capsules, fine granules, granules, powders, etc.) in accordance with the per se known procedures such as those described in, inter alia, JP-A-3 81218, JP-B-1 12727 (1989), JP-B-63 51123 (1988), and JP-B-1 39405 (1989), or any pharmaceutical procedures analogous thereto.

Among others, preferred dosage forms are tablets each containing 30 mg or more of idebenone, capsules each containing 30 mg or more of idebenone, fine granules containing 30 mg or more of idebenone per packet, and granules containing 30 mg or more of idebenone per packet.

The pharmaceutical composition for treating or preventing Alzheimer's disease and the pharmaceutical composition for inhibiting the progression of dementia, of the present invention are useful for treating or preventing and/or inhibiting the progression of Alzheimer's disease, particularly in patients with senile dementia of the Alzheimer type and patients with Alzheimer's disease. Moreover the above compositions are useful for treating neurological symptoms after stroke, vascular type dementia, and so forth.

The pharmaceutical composition for treating or preventing Alzheimer's disease and the pharmaceutical composition for inhibiting the progression of dementia, of the present invention are of low toxicity and can be safely administered to humans by the oral route.

The dosage of the pharmaceutical composition for treating or preventing Alzheimer's disease or the pharmaceutical composition for inhibiting the progression of dementia, of the present invention is dependent on each dosage form, the kinds of active ingredients, and the method of administration.

The dosage of idebenone is about 90 mg to about 3000 mg/day, preferably about 180 mg to about 1500 mg/day, more preferably about 270 mg to about 1440 mg/day. The dosage is adjusted according to the symptomatic severity of Alzheimer's disease.

The dosage of the compound having acetylcholinesterase inhibitory activity is dependent on the particular species of compound used but can be somewhere below the threshold at which peripheral nervous symptoms [mainly due to its parasympathetic nerve actions (e.g. diarrhea, tearing, watery mouth, etc.)] will not be expressed in any marked degree. When 3-[1-(phenylmethyl)- 4-piperidinyl]-1-(2,3,4,5-tetrahydro-1H-1-benzazepin-8-yl)-1-propanone fumarate [hereafter referred to as Compound A], for instance, is employed, its dosage is about 1 mg to about 300 mg/day, preferably about 8 mg to about 120 mg/day. When 2,3-dihydro-5,6-dimethoxy-2-[[1-(phenylmethyl)-4-piperidinyl]methyl]-1H-inden-1-one hydrochloride (donepezil, E2020), for instance, is employed, its dosage is about 0.1 mg to about 50 mg/day, preferably about 0.5 mg to about 10 mg/day. When tacrine is employed, its dosage is about 10 mg to about 500 mg/day, preferably about 50 mg to about 200 mg/day. When ipidacrine is employed, its dosage is about 10 mg to about 500 mg/day, preferably about 100 mg to about 300 mg/day. When (S)-3-[1-(dimethylamino)ethyl]phenyl N-ethyl-N-methylcarbamate (rivastigmin, SDZ-ENA-713), for instance, is employed, its dosage is about 1 mg to about 50 mg/day, preferably about 5 mg to about 20 mg/day. When 8-[3 [4-(diethylcarbamoyl) piperazin-1-yl]propyl]-1,3,7-trimethylxanthine hydrochloride (stacofylline, S-9977), for instance, is employed, its dosage is about 1 mg to about 500 mg/day, preferably about 10 mg to about 200 mg/day.

The dosage of the compound having acetylcholinesterase inhibitory activity can be judiciously increased or decreased according to the dosage of idebenone. The relative dosage of such a compound having acetylcholinesterase inhibitory activity is 0.0005 to 1 part by weight per 1 part by weight of idebenone.

The pharmaceutical composition for treating or preventing Alzheimer's disease or the pharmaceutical composition for inhibiting the progression of dementia, of the present invention may be used in combination with various compatible medicaments such as centrally acting drugs [e.g. antianxiety drugs, sleep inducing agents, therapeutic agents for schizophrenia, antiparkinsonian drugs, nootropic agents (e.g. brain circulation improving agents, cerebral metabolism activators, etc.)], antihypertensive agents, antidiabetics, antihyperlipidemic drugs, nutritional supplements (e.g. vitamins, etc.), digestants and absorption promotors, gastrointestinal drugs, and so forth, in addition to idebenone and the compound having acetylcholinesterase inhibitory activity.

BEST MODE FOR CARRYING OUT THE INVENTION

The following test and formulation examples are further illustrative of the present invention.

EXAMPLES

Experimental Example 1

The ameliorative effect of the combined use of idebenone and Compound A on learning deficits was investigated in aged rats.

Methods

Male young (3 months old) rats of the Fischer 344 strain and male aged (27 months old) rats of the Fischer 344 strain were used.

The aged rats were divided into the following four groups.
1) Control group: Saline.
2) Idebenone group: Repeated oral administration of idebenone 3 mg/kg.
3) Compound A group: Repeated oral administration of Compound A 0.3 mg/kg.
4) Combination group: Repeated oral administration of idebenone 3 mg/kg and compound A 0.3 mg/kg.

In the combination group, idebenone was administered 30 minutes after administration of Compound A.

Passive avoidance learning test was started on day 14 of treatment, and Morris water maze learning test on day 20 of treatment.

On each day of experiment, idebenone and Compound A were administered 30 minutes and 1 hour, respectively, before initiation of the trial.

1. Passive Avoidance Learning

The passive avoidance learning test was performed using a chamber consisting of light and dark compartments. Young rats (saline, 10 animals) and aged rats (control group, 9 animals; idebenone group, 7 animals; Compound A group, 8 animals; combination group, 8 animals) were individually placed in the light compartment and 10 seconds later, the sliding door was opened. After a rat moved to the dark compartment, the rat was kept there for about 10 seconds with the door closed. One to two hours after the habituation trial, acquisition trial was performed.

In the acquisition trial, after a rat moved to the dark compartment, afoot shock (0.4 mA, 3 seconds) was given through the grid floor. Retention trials were performed 24 hours after acquisition trials.

In each trial, the latency from opening of the slide door till the animal moved to the dark compartment (step-through latency) was measured.

2. Morris Water Maze Learning

The water maze learning test was performed on young rats (saline, 10 animals) and aged rats (control group, 7 animals; idebenone group, 6 animals; Compound A group, 6 animals; combination group, 6 animals).

In pretraining which was performed for swimming training and motivation for escaping from water, four trials were performed using a water bath, 80 cm in diameter, in a condition that the platform was visible. From the following day, using a water bath, 120 cm in diameter, learning trials, one session (four trials) per day, were performed with the platform being placed below the water.

Results

1. Passive Avoidance Learning

There were no differences in latencies in the habituation trial and acquisition trial between aged and young rats. Drug treatment had no influence on the latencies.

In the retention trials performed 24 hours after shock loading, the idebenone group and the Compound A group tented to show improvements in learning deficit in aged rats but the effect was not significant. On the other hand, the combination group showed significant improvement compared with the control group [FIG. 1].

These results indicate that treatment with idebenone alone or Compound A alone did not improve passive avoidance learning deficit in aged rats, whereas the combination of idebenone and Compound A improved the learning deficit in aged rats.

2. Water Maze Learning

There was no difference between the groups in the latency to find the platform in the pretraining for the purposes of swimming training and motivation for escaping from the water.

The average latencies to find the platform in the subsequent water maze learning tests are shown in FIG. 2, with four trials a day being taken as one session.

In the control group, the latency was little shortened by training. The idebenone group showed a slight tendency toward improvement in water maze learning deficit in the latter period of training. The Compound A group showed a decrease in the latency on day 2 of the experiment but did not differ from the control group on day 3. On the other hand, the combination group showed a marked improvement on days 2 and 3 of the experiment.

The analysis of the results in FIG. 2 by two-way analysis of variance showed significant differences ($F(4,30)=9.49$, $P<0.01$) between the groups and an effect of training ($F(2, 60)=7.06$, $P<0.01$).

Group comparison of average latencies to find the platform for all trials revealed that the control group showed significant prolongation as compared with young rats ($P<0.01$), indicating an overt learning deficit. The idebenone group and the Compound A group did not show significant shortening of average latency compared with the control group, while the combination group showed significant shortening of latency compared with the control group ($P<0.01$).

These results indicate that treatment with idebenone alone or Compound A alone did not improve water maze learning deficit in aged rats, whereas combination of idebenone and Compound A improved water maze learning deficit in aged rats.

Experimental Example 2

The ameliorative effect of the combined use of idebenone and donepezil (hereinafter referred to as Compound B) on learning deficits was investigated in aged rats.

Methods

Male young (3 months old) rats of the Fischer 344 (F344) strain and male aged (27 months old) rats of the F344 strain were used.

The aged rats were divided into the following four groups.
1) Control group: Repeated administration of saline.
2) Idebenone group: Repeated oral administration of idebenone 3 mg/kg.
3) Compound B group: Repeated oral administration of Compound B 0.3 mg/kg.
4) Combination group: Repeated oral administration of idebenone 3 mg/kg and Compound B 0.3 mg/kg.

In the combination group, idebenone was administered 30 minutes after administration of Compound B.

Passive avoidance learning test was started on day 14 of treatment, and Morris water maze learning test on day 20 of treatment.

On each day of experiment, idebenone and Compound B were administered 30 minutes and 1 hour, respectively, before initiation of the trial.

1. Passive Avoidance Learning

The passive avoidance learning test was performed using a chamber consisting of light and dark compartments. Young rats (saline, 10 animals) and aged rats (control group, 10 animals; idebenone group, 10 animals; Compound B group, 10 animals; combination group, 10 animals) were individually placed in the light compartment and 10 seconds later, the sliding door was opened. After a rat moved to the dark compartment, the rat was kept there for about 10 seconds with the door closed. One to two hours after the habituation trial, acquisition trial was performed.

In the acquisition trial, after a rat moved to the dark compartment, afoot shock (0.4 mA, 3 seconds) was given through the grid floor. Retention trials were performed 24 hours after acquisition trials.

In each trial, the latency from opening of the slide door till the animal moved to the dark compartment (step-through latency) was measured.

2. Morris Water Maze Learning

Same animals used in the passive avoidance test were subjected for the water maze task. However, some rats could not swim well in the water tank, thus they were excluded in the water maze task. The water maze learning test was performed on young rats (saline, 10 animals) and aged rats (control group, 9 animals; idebenone group, 9 animals; Compound B group, 8 animals; combination group, 8 animals).

In pretraining which was performed for swimming training and motivation for escaping from water, four trials were performed using a water bath, 80 cm in diameter, in a condition that the platform was visible. From the following day, using a water bath, 120 cm in diameter, learning trials, one session (four trials) per day, were performed with the platform being placed below the water.

Results

1. Passive Avoidance Learning

The control group showed a significant decrease in the avoidance time as compared with the young group. The idebenone group or the Compound B group tended to show improvement of the learning deficit in aged rats. On the other hand, the combination group showed a significant improvement compared with the control group [FIG. 3].

These results indicate that the combination of idebenone and Compound B improved the learning deficit in aged rats.

2. Water Maze Learning

There was no difference between the groups in the latency to find the platform in the pretraining for the purposes of swimming training and motivation for escaping from the water.

The average latencies to find the platform in the subsequent water maze learning tests are shown in FIG. 4, with four trials a day being taken as one session.

In the water maze task, the control group showed a significant prolongation of latency to find platform submerged in the water compared with the young rats. The idebenone group and the Compound B group showed a slight tendency toward improvement in water maze learning deficit. However, the combination group showed a significant shortening of latency compared with the control group.

These results indicate that combination of idebenone and Compound B improved water maze learning deficit in aged rats.

Preparation Example 1

Production of tablets containing 90 mg of idebenone

| | |
|---|---|
| Idebenone | 90,000 g |
| Lactose (EP) | 233,186 g |
| Gelatinized starch | 11,210 g |
| Calcium salt of carboxymethyl cellulose (ECG 505) | 67,270 g |
| Magnesium stearate (EP) | 1,120 g |
| Hydroxypropylmethyl cellulose USP (Pharmacoat 606) | 5,573 g |
| Rolyethylene glycol (NF 6000) | 1,393 g |
| Propylene glycol (EP) | 465 g |
| Talc (EP) | 1,858 g |
| Titanium oxide (EP E171) | 2,786 g |
| Red Color 30 (E172) | 139 g |
| Total | 415,000 g |

After idebenone and water were added to, and kneaded with, the above excipients for pharmaceutical preparations, the mixture was dried. To this dry kneaded product, the above disintegrants and lubricant were added, followed by uniform mixing, after which the whole mixture was compressed using a compressive tableting machine to yield 1,000,000 tablets 11 mm in diameter, 4.3 mm in thickness and 415 mg in weight which contained 90 mg of idebenone per tablet.

Preparation Example 2

Production of tablets containing 120 mg of idebenone

| | |
|---|---|
| Idebenone | 120,000 g |
| Lactose (EP) | 203,186 g |
| Gelatinized starch | 11,210 g |
| Calcium salt of carboxymethyl cellulose (ECG 505) | 67,270 g |
| Magnesium stearate (EP) | 1,120 g |
| Hydroxypropylmethyl cellulose USP (Pharmacoat 606) | 5,573 g |
| Rolyethylene glycol (NF 6000) | 1,393 g |
| Propylene glycol (EP) | 465 g |
| Talc (EP) | 1,858 g |
| Titanium oxide (EP E171) | 2,786 g |
| Red Color 30 (E172) | 139 g |
| Total | 415,000 g |

After idebenone and water were added to, and kneaded with, the above excipients for pharmaceutical preparations, the mixture was dried. To this dry kneaded product, the above disintegrants and lubricant were added, followed by uniform mixing, after which the whole mixture was compressed using a compressive tableting machine to yield 1,000,000 tablets 11 mm in diameter, 4.3 mm in thickness and 415 mg in weight which contained 120 mg of idebenone per tablet.

Preparation Example 3

Production of tablets containing Compound A

| | |
|---|---|
| Compound A | 1 g |
| Lactose | 19 g |
| Corn starch | 50 g |
| Magnesium stearate | 2 g |
| Total | 72 g |

The above compound A, lactose, and corn starch (20 g) were blended. This blend was granulated with a paste prepared from corn starch (15 g) and water (25 ml). After addition of corn starch (15 g) and magnesium stearate (2 g), the granulation was compressed with a tablet machine to provide 2000 tablets (3 mm in diameter) each containing 0.5 mg of compound A.

INDUSTRIAL APPLICABILITY

The mixture, combination dosage form, or concomitant therapy which comprises idebenone in combination with a compound having acetylcholinesterase inhibitory activity can be safely administered or applied to dementing subjects, particularly patients with senile dementia of Alzheimer type and patients with Alzheimer's disease, with a great success in ameliorating various symptoms of dementia.

We claim:

1. A pharmaceutical composition which comprises syneraistically effective amounts of idebenone in combination with a compound having acetylcholinesterase inhibitory activity.

2. A composition of claim 1, wherein the compound having acetylcholinesterase inhibitory activity is a compound of the formula:

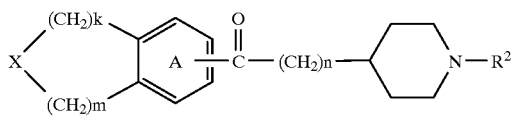

wherein X represents (i) R¹—N< wherein $R^1$ represents hydrogen, a hydrocarbon group which may be substituted or acyl which may be substituted, (ii) oxygen or (iii) sulfur;

$R^2$ represents hydrogen or a hydrocarbon group which may be substituted;

ring A represents a benzene ring which may be substituted;

k represents an integer of 0 to 3;

m represents an integer of 1 to 8; and n represents an integer of 1 to 6, or a salt thereof.

3. A composition of claim 1, wherein the compound having acetylcholinesterase inhibitory activity is 3-[1-(phenylmethyl)-4-piperidinyl]-1-(2,3,4,5-tetrahydro-1H-1-benzazepin-8-yl)-1-propanone fumarate.

4. A composition of claim 1, wherein the compound having acetylcholinesterase inhibitory activity is 2,3-dihydro-5,6-dimethoxy-2-[[1-(phenylmethyl)-4-piperidinyl]methyl]-1H-inden-1-one hydrochloride, (S)-3-[1-(dimethylamino)ethyl]phenyl N-ethyl-N-methylcarbamate or 9-amino-2,3,5,6,7,8-hexahydro-1Hcyclopenta[b]quinoline.

5. A method for treating or preventing Alzheimer's disease in a mammal in need thereof, which comprises administering to such mammal synergistically effective amounts of idebenones in combination with a compound having acetylcholinesterase inhibitory activity.

* * * * *